United States Patent [19]

Amos et al.

[11] Patent Number: 5,578,720
[45] Date of Patent: Nov. 26, 1996

[54] LORACARBEF HYDROCHLORIDE C1-C3 ALCOHOL SOLVATES AND USES THEREOF

[75] Inventors: Jane G. Amos, Mooresville; Perry C. Heath, Indianapolis; Douglas E. Prather, Brownsburg; John E. Toth, Indianapolis, all of Ind.

[73] Assignee: Eli Lilly and Company, Indianapolis, Ind.

[21] Appl. No.: 444,124

[22] Filed: May 18, 1995

Related U.S. Application Data

[62] Division of Ser. No. 77,305, Jun. 15, 1993.

[51] Int. Cl.$^6$ ................................................. C07D 221/00
[52] U.S. Cl. ............................................................. 540/205
[58] Field of Search ............................................. 540/205

[56] References Cited

U.S. PATENT DOCUMENTS

| | | | |
|---|---|---|---|
| 4,316,958 | 2/1982 | Hirata et al. | 435/119 |
| 4,332,896 | 6/1982 | Hashimoto et al. | 435/119 |
| 4,335,211 | 6/1982 | Hashimoto et al. | 435/119 |
| 4,775,751 | 10/1988 | McShane | 540/230 |
| 4,977,257 | 12/1990 | Eckrich et al. | 540/205 |
| 5,057,607 | 10/1991 | Zmijewski, Jr. et al. | 540/364 |
| 5,352,782 | 10/1994 | Nist et al. | 540/205 |
| 5,374,719 | 12/1994 | Plocharczyk et al. | 540/205 |
| 5,399,686 | 3/1995 | Henning et al. | 540/205 |
| 5,412,094 | 5/1995 | Amos et al. | 540/205 |

FOREIGN PATENT DOCUMENTS

| | | |
|---|---|---|
| 0007689 | 6/1980 | European Pat. Off. . |
| 0311366 | 10/1988 | European Pat. Off. . |
| 0369686 | 11/1989 | European Pat. Off. . |
| 0369687 | 5/1990 | European Pat. Off. . |
| 0439353A1 | 1/1992 | European Pat. Off. . |
| 0439353 | 1/1992 | European Pat. Off. . |

*Primary Examiner*—Mukund J. Shah
*Assistant Examiner*—Brenda Coleman
*Attorney, Agent, or Firm*—Kathleen R. S. Page; Thomas G. Plant

[57] ABSTRACT

This invention provides for crystalline hydrochloride $C_1$-$C_3$ alcohol solvate forms of the compound of formula (I):

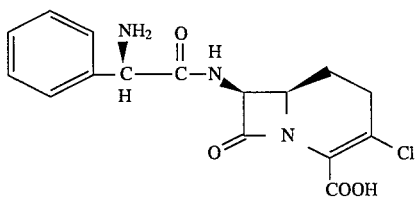

In particular, crystalline hydrochloride ethanol, methanol, and propanol solvates are disclosed.

6 Claims, No Drawings

LORACARBEF HYDROCHLORIDE C1-C3 ALCOHOL SOLVATES AND USES THEREOF

This application is a division of application Ser. No. 08/077,305 filed Jun. 15, 1993.

BACKGROUND OF THE INVENTION

This invention relates to crystalline loracarbef hydrochloride $C_1$–$C_3$ alcohol solvates and uses thereof.

The β-lactam antibiotic of the formula (I)

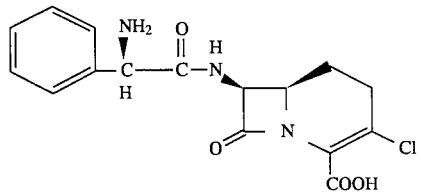

is the potent orally active antibiotic known as loracarbef. This antibiotic is described, for example, by Hashimoto et al, in U.S. Pat. No. 4,335,211, issued Jun. 15, 1982.

The above compounds come in various forms, including the crystalline monohydrate form, which is disclosed in European Patent Publication 0,311,366 having a publication date of Apr. 12, 1989. The crystalline dihydrate form of loracarbef is disclosed in European Patent Publication 0,369,686, having a publication date of May 23, 1990. Other known solvate forms of the compound are disclosed in Eckrich et al. U.S. Pat. No. 4,977,257 issued Dec. 11, 1990 and Pfeiffer et al., European Patent Publication No. 0,439,353, having a publication date of Jul. 31, 1991. The Pfeiffer et al. reference discloses the crystalline hydrochloride form of loracarbef.

Continuous efforts are being made for alternative methods for isolation, purification and recovery of loracarbef to increase the possible total yield.

SUMMARY OF THE INVENTION

This invention provides for crystalline hydrochloride $C_1$–$C_3$ alcohol solvate forms of the compound of formula (I):

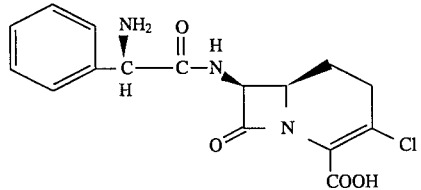

In particular, crystalline hydrochloride ethanol, methanol, and propanol solvates are disclosed. Also disclosed are processes for preparing and using the above compounds.

DESCRIPTION OF THE INVENTION

The present invention is directed to crystalline hydrochloride $C_1$–$C_3$ alcohol solvates of the compound of formula (I):

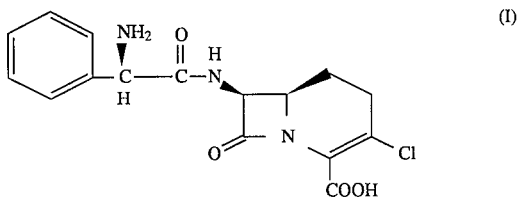

In the present solvates of formula (I) the C-2' asymmetric center has the R absolute configuration. Furthermore, the solvates may encompass the Zwitterionic form of the compound of formula (I).

A preferred embodiment of the invention is the crystalline hydrochloride ethanol solvate of the compound of formula (I) exhibiting the X-ray powder diffraction pattern of Table 1:

TABLE 1

| d | $I/I_1$ |
|---|---|
| 19.92 | –2.0 |
| 9.77 | 100.0 |
| 7.39 | 58.8 |
| 6.17 | 16.3 |
| 5.65 | 40.9 |
| 5.05 | 58.9 |
| 4.85 | 21.2 |
| 4.65 | 0.7 |
| 4.49 | 66.4 |
| 4.37 | 1.5 |
| 4.27 | 13.2 |
| 4.00 | 10.2 |
| 3.89 | 3.1 |
| 3.83 | 0.8 |
| 3.69 | 38.4 |
| 3.62 | 0.7 |
| 3.52 | 91.0 |
| 3.39 | 7.5 |
| 3.35 | 7.9 |
| 3.27 | 26.0 |
| 3.20 | –0.6 |
| 3.14 | 13.9 |
| 3.09 | 12.7 |
| 2.97 | 6.4 |
| 2.87 | 5.6 |
| 2.82 | 6.1 |
| 2.74 | 6.2 |
| 2.70 | 6.4 |
| 2.64 | 10.1 |
| 2.60 | 2.3 |

The diffraction pattern in Table 1 was obtained with a nickel-filtered copper radiation (Cu:Ni) of wavelength γ=1.5406 Å and are uncorrected. The interplanar spacings are in the column marked "d" and are in Angstroms and the relative intensities are in the column marked "$I/I_1$".

Another embodiment of the instant invention is the crystalline hydrochloride methanol solvate of the compound of formula (I) exhibiting the X-ray powder diffraction pattern set forth below in Table 2.

TABLE 2

| d | $I/I_1$ |
|---|---|
| 17.9471 | 21.60 |
| 13.5209 | 100.00 |
| 9.4758 | 6.22 |
| 9.0915 | 6.69 |
| 9.0915 | 6.69 |

TABLE 2-continued

| d | I/I$_1$ |
|---|---|
| 7.3142 | 3.87 |
| 7.1382 | 5.75 |
| 6.8539 | 18.54 |
| 6.6895 | 6.22 |
| 5.9775 | 5.63 |
| 5.7694 | 4.46 |
| 5.6608 | 5.40 |
| 5.5616 | 13.97 |
| 5.3491 | 7.16 |
| 5.1413 | 3.29 |
| 5.0208 | 6.10 |
| 4.7465 | 5.87 |
| 4.5602 | 4.46 |
| 4.4469 | 4.58 |
| 4.3384 | 5.05 |
| 4.3384 | 5.05 |
| 4.1200 | 10.80 |
| 3.8563 | 5.87 |
| 3.7084 | 7.98 |
| 3.6379 | 12.44 |
| 3.5872 | 13.38 |
| 3.5273 | 8.10 |
| 3.4491 | 12.91 |
| 3.3684 | 7.51 |
| 3.1719 | 7.98 |
| 3.1132 | 5.63 |
| 2.9748 | 5.16 |

The X-ray data in Table 2 was collected employing the same instrument parameters as used in collecting the data in Table 1.

Another embodiment of the invention is the crystalline loracarbef hydrochloride 1-propanol solvate exhibiting the x-ray powder diffraction pattern set forth below in Table 3.

TABLE 3

| d | I/I$_1$ |
|---|---|
| 10.0767 | 100.0 |
| 9.7099 | 7.75 |
| 8.1380 | 3.96 |
| 7.5370 | 42.41 |
| 6.2587 | 5.54 |
| 5.8976 | 7.91 |
| 5.7412 | 17.72 |
| 5.6398 | 11.23 |
| 5.4127 | 3.80 |
| 5.2174 | 5.54 |
| 5.1075 | 45.41 |
| 4.9370 | 7.59 |
| 4.8905 | 9.49 |
| 4.5360 | 37.03 |
| 4.3921 | 12.34 |
| 4.2845 | 7.75 |
| 4.0913 | 11.55 |
| 3.7735 | 11.08 |
| 3.7132 | 16.46 |
| 3.6574 | 18.04 |
| 3.5853 | 21.36 |
| 3.5444 | 27.22 |
| 3.4696 | 7.59 |
| 3.3750 | 12.97 |
| 3.2862 | 14.72 |
| 3.2369 | 6.96 |
| 3.1533 | 10.76 |
| 3.0222 | 5.22 |
| 2.9859 | 6.01 |
| 2.9624 | 6.65 |
| 2.8638 | 6.49 |
| 2.8268 | 5.22 |
| 2.7363 | 6.96 |
| 2.6960 | 6.33 |
| 2.6186 | 6.01 |

The X-ray data in Table 3 was collected employing the same instrument parameters used to collect the data in Table 1.

The loracarbef hydrochloride $C_1$–$C_3$ alcohol solvates can be prepared by suspending any form of the compound, for example, the bis (DMF) solvate form, in ethanol and concentrated or anhydrous hydrochloric acid. After the addition of the solvent and acid, the mixture is maintained at a temperature of about 0° to about 25° C. to facilitate precipication. The precipitate can then be filtered, washed with the particular alcohol, and dried to yield the loracarbef hydrochloride alcohol solvate. The amount of alcohol used should be an amount of 7 to about 14 ml per gram of loracarbef. The amount of hydrochloric acid used should be in a slight molar excess, or in the amount of 1 to about 1.2 equivalents.

As noted above, the loracarbef hydrochloride alcohol solvates are useful as intermediates to the loracarbef monohydrate and especially as purification tools. The monohydrate may be prepared by first suspending any of the alcohol solvates in either the particular alcohol solvent contained in the compound, dimethylformamide and/or water. The pH of the mixture is lowered, if needed, to induce dissolution using a suitable acid such as hydrochloric, sulfuric, or hydrobromic acids. The pH of the mixture is then raised by the addition of a base such as sodium hydroxide, ammonium hydroxide or triethylamine. The product is filtered, washed with the particular alcohol or DMF, and dried or taken directly into the monohydrate conversion. For example, the hydrochloride alcohol solvate may be slurried in ethanol, followed by addition of a base to include dissolution to result in the ethanolate form of loracarbef. Thereafter, the ethanolate may be slurried in water at a temperature of about 50° C. to result in formation of the monohydrate.

An important use for the solvates is in purifying enzymatic reaction mixtures. When enzymatic acylation reactions are run according to those described in U.S. Pat. Nos. 4,316,958, 4,332,896, or 4,335,211, there remains as much as 30–35% D-phenylglycine. By precipitating the hydrochloride $C_1$–$C_3$ alcohol solvate, that level can be markedly reduced, and in the case of the hydrochloride ethanol solvate, the D-phenylglycine can be removed completely.

EXPERIMENTALS

Example 1

Loracarbef Hydrochloride Ethanol Solvate

A slurry of crystalline bis(N,N'-dimethylformamide)solvate of 7β-[2'-(R)-2'-phenyl-2'-aminoacetamido]-3-chloro-3-(1-carba(dethia)cephem)-4-carboxylic acid (27.74 g, 18.84 bg (mw=349.8), 53.9 mmole;potency=67.9%, diazotozable amine=263 ppm)) in 120 ml of ethanol was treated with a 2.63M solution of HCl(g) in EtOH (21.7 ml, 57.1 mmole, 1.06 eq). The resulting clear yellow solution was cooled to ice bath temperature for two hours and seeded with the titled product. Crystallization began immediately and after thirty minutes, the titled product was collected by filtration, washed with ethanol and dried overnight in an air oven at 45° C.; yield=23.46 g (93%) based on a HPLC potency of 74.7%; KF=0.85% and diazotizable amine=140 ppm. mp 177° C. decomp.;

Combustion Analysis: Theory $C_{16}H_{17}N_3O_4Cl_2$·1.3 $C_2H_5OH$: C, 50.08; H, 5.60; N, 9.42; Found: C, 49.18; H, 5.67; N, 9.39;

UV(EtOH) 264 nm (10,000);

IR(KBr)3440(b),3200(b),2600,1780,1700,1540,1370, 1320,1 240 cm$^{-1}$;

$[a]_D$(25° C., H$_2$O,c=1.0)=+32.92°;FAB(DMSO)M$^+$=350, 352;

| X-Ray Crystal Diffraction Pattern: | |
| --- | --- |
| d | I/I$_1$ |
| 19.92 | −2.0 |
| 9.77 | 100.00 |
| 7.39 | 58.8 |
| 6.17 | 16.3 |
| 5.65 | 40.9 |
| 5.05 | 58.9 |
| 4.85 | 21.2 |
| 4.65 | 0.7 |
| 4.49 | 66.4 |
| 4.37 | 1.5 |
| 4.27 | 13.2 |
| 4.00 | 10.2 |
| 3.89 | 3.1 |
| 3.83 | 0.8 |
| 3.69 | 38.4 |
| 3.62 | 0.7 |
| 3.52 | 91.0 |
| 3.39 | 7.5 |
| 3.35 | 7.9 |
| 3.27 | 26.0 |
| 3.20 | −0.6 |
| 3.14 | 13.9 |
| 3.09 | 12.7 |
| 2.97 | 6.4 |
| 2.87 | 5.6 |
| 2.82 | 6.1 |
| 2.74 | 6.2 |
| 2.70 | 6.4 |
| 2.64 | 10.1 |
| 2.60 | 2.3 |

The diffraction pattern was obtained with nickel-filtered copper radiation (Cu:Ni) of wavelength λ=1.5406 Å. The interplanar spacings are in the column marked "d" and are in Angstroms and the relative intensities are in the column marked "I/I1."

Example 2

Crystalline Loracarbef Monohydrate

To a solution of Na$_4$EDTA (350 mg) in 85 ml of water was added material obtained from Example 1 (13.4 g, 10.0 bg (MW=349.8), 28.6 mmole). After fifteen minutes of stirring, 1.0 ml of concentrated HCl was added to complete dissolution (pH=1.37). To this was added Darco-G50 (350 mg), and after stirring fifteen minutes, the reaction mixture was filtered through a Hyflo pad and the pad rinsed with 15 ml of water. The combined filtrate and washing were heated to 50° C. with stirring and triethylamine (1.2 ml) was added at rate of 3.9 ml/hr to give a pH=1.7. The solution was seeded with Loracarbef monohydrate crystal and after stirring a further thirty minutes at 50° C., the addition of triethylamine was resumed at a rate of approx 3.9 ml/hr until the reaction mixture reached a pH=4.7 (3.6 ml of triethylamine were added). After stirring thirty minutes further at pH=4.7 and 50° C., the reaction mixture was filtered on a buchner funnel and the titled product washed with 17 ml of water. The wet cake was reslurried in 100 ml of water at room temperature, collected on a filter and dried overnight in an air oven at 45° C. to give 7.02 g (70.2%) of the titled product; potency= 100%; KF=4.09%; triethylamine=0.01%, diazotizable amine=38; x-ray diffraction pattern confirmed monohydrate.

Example 3

Crystalline Loracarbef Monohydrate

A. Isolation of Enzymatic Acylation

An acylation reaction proceeding substantially according to U.S. Pat. Nos. 4,316,958, 4,332,896, and 4,335,211 is run and thereafter the acylation solution is removed from the flask by vacuum through a glass sparger. The enzyme beads are washed with MilliQ water. These washes are combined with the acylation solution and extracted 2× with CH$_2$C$_{12}$. The aqueous phase is HyFlo filtered. The HyFlo filter pad is washed twice with minimal volumes of phosphate buffer. Combined volume of extracted acylation solution and washes are sampled in triplicate for HPLC analysis.

The pH of the aqueous layer is lowered to 4.6–4.9 with concentrated HCl. An equal volume of ethyl alcohol is added dropwise over 1.5 hr. Precipitation occurs after 10 minutes and is thick. After the addition is complete, the mixture is stirred for several hours at room temperature and then for several hours at 0°–5° C. The product is filtered and washed with ethyl alcohol and dried overnight at 45° C. The product contains approximately 62–68% loracarbef as the monohydrate and 30–35% D-phenylglycine. The potency is obtained by running triplicate samples on the HPLC. The K.F. is 5–8%. The % yield from starting nucleus is 73–79%.

B. Hydrochloride Ethanolate Salt of Loracarbef

The HCl salt of loracarbef is obtained from the loracarbef isolated from the enzymatic acylation. The loracarbef crystal (60–75% potency as the monohydrate, containing 22–40% D-phenyl glycine) is slurried in 10 volumes of ethanol. An equivalent of concentrated HCl, based on the potency of loracarbef and D-phenyl glycine, is for complete dissolution. Additional HCl (0.6 eq.) is added. The pH is 0.60–0.80. The clear solution is seeded with loracarbef hydrochloride ethanolate to initiate crystallization. The HCl crystallizes slowly over several hours at room temperature. After stirring for 2 hours at room temperature, the crystallization mixture is cooled to 0°–5° C. and stirred for one hour. The mixture is filtered, washed with ethanol, and dried under vacuum at 40° C. overnight to yield a white, crystalline solid with a potency of 90°–99% as loracarbef hydrochloride ethanolate. No D-phenyl glycine is detected by HPLC. The yields using the above procedure range from 80–95%.

C. Slurry Conversion of Loracarbef Hydrochloride Ethanol Solvate to Loracarbef Ethanolate.

Loracarbef hydrochloride ethanolate (5.10 g) was slurried in 75 ml ethanol at room temperature. Triethylamine (1.54 ml, 1.0 eq.) was added dropwise to obtain a pH of 4.6–4.8. The slurry became thick within 30 minutes to indicate that the hydrochloride ethanolate salt was being converted to loracarbef ethanolate. The slurry was stirred for 2 hours at room temperature, filtered, washed with ethanol, and dried under vacuum at 40° C.

Actual Yield—4.10 g.

Theoretical Yield—4.06 g. % Yield—98.1%

D. Conversion of Loracarbef Ethanolate to Loracarbef Monohydrate

Loracarbef ethanolate, (4.0 g, 97.1% potency), was slurried in 56 ml of water (containing 0.004 eq sodium, ~0.02 g editate) at 50° C. for 2 hours. Within 30 minutes the slurry became very thick, indicating conversion to monohydrate.

The product was vacuum filtered, washed with a minimum amount of water, and dried in a 40° C. vacuum oven. X-ray-confirmed as monohydrate.

Actual Yield—2.78 g,

Theoretical field—3.88 g % Yield—72.4%

Example 4

Loracarbef Hydrochloride Ethanol Solvate

Loracarbef DMF disolvate (4.5 g, 68.7% potency) was suspended in 45 ml EtOH. Added 0.80 ml concentrated HCl to obtain a clear solution. Cooled to 10° C. Product began to precipitate within 50 minutes. Maintained a 10° C. temperature and stirred for 2 hours. Filtered and washed with EtOH. Dried product under vacuum at 40° C.

Actual yield—2.82 g
Theoretical yield—3.41 g % yield—82.7%

Example 5

Loracarbef Hydrochloride Ethanol Solvate

Loracarbef DMF disolvate (1.0 g) was suspended in 10 ml EtOH. Added 0.33 ml conc. HCl. A clear solution was obtained. Within 30 minutes no crystallization had begun. Seeded with the titled product and within 5 minutes crystallization began. Stirred at room temperature (20°–28° C.) for 2 hours. Filtered (very granular) easily. Washed with ethanol. Dried in a 40° C. vacuum oven.

Actual yield—0.52 g
Theoretical yield—0.75 g % yield—69.3%

Example 6

Loracarbef Hydrochloride Methanolate

Loracarbef dihydrate (5 g) was added to 20 ml of methanol and 1.34 ml of concentrate hydrochloride acid at room temperature. The solution was stirred for approximately 15 minutes and a nitrogen purge was used to evaporate the solvent overnight. The titled produce had the following X-ray diffraction pattern:

| d | $I/I_1$ |
|---|---|
| 17.9471 | 21.60 |
| 13.5209 | 100.00 |
| 9.4758 | 6.22 |
| 9.0915 | 6.69 |
| 9.0915 | 6.69 |
| 7.3142 | 3.87 |
| 7.1382 | 5.75 |
| 6.8539 | 18.54 |
| 6.6895 | 6.22 |
| 5.9775 | 5.63 |
| 5.7694 | 4.46 |
| 5.6608 | 5.40 |
| 5.5616 | 13.97 |
| 5.3491 | 7.16 |
| 5.1413 | 3.29 |
| 5.0208 | 6.10 |
| 4.7465 | 5.87 |
| 4.5602 | 4.46 |
| 4.4469 | 4.58 |
| 4.3384 | 5.05 |
| 4.3384 | 5.05 |
| 4.1200 | 10.80 |
| 3.8563 | 5.87 |
| 3.7084 | 7.98 |
| 3.6379 | 12.44 |
| 3.5872 | 13.38 |
| 3.5273 | 8.10 |
| 3.4491 | 12.91 |
| 3.3684 | 7.51 |
| 3.1719 | 7.98 |
| 3.1132 | 5.63 |
| 2.9748 | 5.16 |

Example 7

Loracarbef Hydrochloride 1-Propanaol solvate

Loracarbef methanolate (5 g) is added to 50 ml of 1-propanol and 1.34 ml of concentrated hydrochloride acid. The solution is stirred at room temperature for approximately 45 minutes and is stripped to solids and placed in the freezer, with large rhomboid crystals formed. The mixture is dried overnight at room temperature in a vacuum oven and the crystals yellowed. The weight yield is 5.16 grams and the X-ray diffraction pattern of the titled product above is as follows:

| d | $I/I_1$ |
|---|---|
| 10.0767 | 100.00 |
| 9.7099 | 7.75 |
| 8.1380 | 3.96 |
| 7.5370 | 42.41 |
| 6.2587 | 5.54 |
| 5.8976 | 7.91 |
| 5.7412 | 17.72 |
| 5.6398 | 11.23 |
| 5.4127 | 3.80 |
| 5.2174 | 5.54 |
| 5.1075 | 45.41 |
| 4.9370 | 7.59 |
| 4.8905 | 9.49 |
| 4.5360 | 37.03 |
| 4.3921 | 12.34 |
| 4.2845 | 7.75 |
| 4.0913 | 11.55 |
| 3.7735 | 11.08 |
| 3.7132 | 16.46 |
| 3.6574 | 18.04 |
| 3.5853 | 21.36 |
| 3.5444 | 27.22 |
| 3.4696 | 7.59 |
| 3.3750 | 12.97 |
| 3.362 | 14.72 |
| 3.2369 | 6.96 |
| 3.1533 | 10.76 |
| 3.0222 | 5.22 |
| 2.9859 | 6.01 |
| 2.9624 | 6.65 |
| 2.8638 | 6.49 |
| 2.8268 | 5.22 |
| 2.7363 | 6.96 |
| 2.6960 | 6.33 |
| 2.6186 | 6.01 |

Example 8

Loracarbef Hydrochloride Ethanolate

A 1 L 4 NK RB flask was set up with a pH probe, gas addition subsurface tube, thermometer, $N_2$ purge, and gas vent. Loracarbef (containing 26.4% D-PGOH) product from an enzymatic acylation, 150 g (0.30 eq of loracarbef, 0.26 eq D-PGOH) was added to the flask. Next, 2B-3 alcohol (750 ml) was added. The contents were stirred at 20° to 25° C. for 10 to 15 minutes. The initial pH was 5.3. The pH was lowered to 0.6 to 0.8 over 20 to 30 minutes using anhydrous HCl gas. At pH 0.95 there was a slurry to slurry conversion to HCl salt. The mixture exothermed to 44° C. during the HCl addition. The pH was adjusted slightly during this time by careful addition of HCl gas. The final pH was 0.80. The total amount of HCl used was 19.9 G. The slurry was then cooled to −10° to −5° C. and stirred for 2 hours. The produce was filtered and washed with 2B-3 alcohol. The product was dried in a 40° C. vacuum oven for 18 hours.

Actual Yield—137.96 G, potency as loracarbef monohydrate—79.6% theoretical Yield—111.6 g as loracarbef monohydrate % yield—98.4% No D-PGOH was detected by HPLC Example 9

Loracarbef Ethanolate

Loracarbef Hydrochloride Ethanolate (20 g, 0.044 moles) was dissolved in $H_2O$ (25 ml) with stirring at room temperature. Concentrated HCl was added (with stirring) to obtain a clear solution. The pale yellow solution was stirred for 10 minutes at room temperature, filtered through hyflo, and washed with $H_2O$ (25 ml). Ethanol, 2B-3 (240 ml) was added dropwise at room temperature over 1 hour. A white precipitate formed within 10 minutes. Triethylamine (1.0 equivalent, 6.18 ml) was dissolved in 2B-3 ethanol (60 ml) and added dropwise to the loracarbef hydrochloride ethanolate slurry at room temperature over 1.5 hour. The pH was adjusted to 4.6 to 4.8 with either triethylamine or concentrated HCl, as needed. The slurry was stirred at room temperature for 2 hours, filtered, and washed with 2B-3 ethanol (50 to 60 ml) The product was dried under vacuum at 40° C. The yield was 98.2%.

Actual yield—16.84 G, 95.2% potency as loracarbef monohydrate, 16.03 BG as loracarbef monohydrate Theoretical yield—16.32 G (as loracarbef monohydrate) yield—98.2

We claim:

1. A crystalline hydrochloride ethanol solvate form of the compound of formula I:

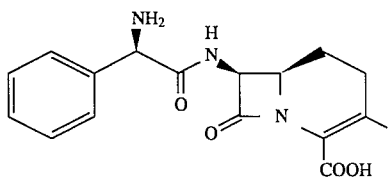

2. A compound of claim 1 which has the following x-ray diffraction pattern obtained with a nickel-filtered copper radiation of $\lambda=1.5406$ Å wherein d represents the interplanar spacing and $I/I_1$ the relative intensity:

| d | $I/I_1$ |
| --- | --- |
| 19.92 | -2.0 |
| 9.77 | 100.0 |
| 7.39 | 58.8 |
| 6.17 | 16.3 |
| 5.65 | 40.9 |
| 5.05 | 58.9 |
| 4.85 | 21.2 |
| 4.65 | 0.7 |
| 4.49 | 66.4 |
| 4.37 | 1.5 |
| 4.27 | 13.2 |
| 4.00 | 10.2 |
| 3.89 | 3.1 |
| 3.83 | 0.8 |
| 3.69 | 38.4 |
| 3.62 | 0.7 |
| 3.52 | 91.0 |
| 3.39 | 7.5 |
| 3.35 | 7.9 |
| 3.27 | 26.0 |
| 3.20 | -0.6 |
| 3.14 | 13.9 |
| 3.09 | 12.7 |
| 2.97 | 6.4 |
| 2.87 | 5.6 |
| 2.82 | 6.1 |
| 2.74 | 6.2 |
| 2.70 | 6.4 |

-continued

| d | $I/I_1$ |
| --- | --- |
| 2.64 | 10.1 |
| 2.60 | 2.3. |

3. A crystalline hydrochloride methanol solvate form of the compound of formula I:

| d | $I/I_1$ |
| --- | --- |
| 17.9471 | 21.60 |
| 13.5209 | 100.00 |
| 9.4758 | 6.22 |
| 9.0915 | 6.69 |
| 9.0915 | 6.69 |
| 7.3142 | 3.87 |
| 7.1382 | 5.75 |
| 6.8539 | 18.54 |
| 6.6895 | 6.22 |
| 5.9775 | 5.63 |
| 5.7694 | 4.46 |
| 5.6608 | 5.40 |
| 5.5616 | 13.97 |
| 5.3491 | 7.16 |
| 5.1413 | 3.29 |
| 5.0208 | 6.10 |
| 4.7465 | 5.87 |
| 4.5602 | 4.46 |
| 4.4469 | 4.58 |
| 4.3384 | 5.05 |
| 4.3384 | 5.05 |
| 4.1200 | 10.80 |
| 3.8563 | 5.87 |
| 3.7084 | 7.98 |
| 3.6379 | 12.44 |
| 3.5872 | 13.38 |
| 3.5273 | 8.10 |
| 3.4491 | 12.91 |
| 3.3684 | 7.51 |
| 3.1719 | 7.98 |
| 3.1132 | 5.63 |
| 2.9748 | 5.16. |

4. A compound of claim 3 which has the following x-ray diffraction pattern obtained with a nickel-filtered copper radiation of $\lambda 1.5406$ Å wherein d represents the interplanar spacing and $I/I_1$ the relative intensity:

| d | $I/I_1$ |
| --- | --- |
| 17.9471 | 21.60 |
| 13.5209 | 100.00 |
| 9.4758 | 6.22 |
| 9.0915 | 6.69 |
| 9.0915 | 6.69 |
| 7.3142 | 3.87 |
| 7.1382 | 5.75 |
| 6.8539 | 18.54 |
| 6.6895 | 6.22 |
| 5.9775 | 5.63 |
| 5.7694 | 4.46 |
| 5.6608 | 5.40 |
| 5.5616 | 13.97 |
| 5.3491 | 7.16 |
| 5.1413 | 3.29 |
| 5.0208 | 6.10 |
| 4.7465 | 5.87 |
| 4.5602 | 4.46 |
| 4.4469 | 4.58 |
| 4.3384 | 5.05 |
| 4.3384 | 5.05 |
| 4.1200 | 10.80 |
| 3.8563 | 5.87 |
| 3.7084 | 7.98 |
| 3.6379 | 12.44 |

| d | I/I$_1$ |
|---|---|
| 3.5872 | 13.38 |
| 3.5273 | 8.10 |
| 3.4491 | 12.91 |
| 3.3684 | 7.51 |
| 3.1719 | 7.98 |
| 3.1132 | 5.63 |
| 2.9748 | 5.16. |
5. A crystalline hydrochloride propanol solvate form of the compound of formula I:
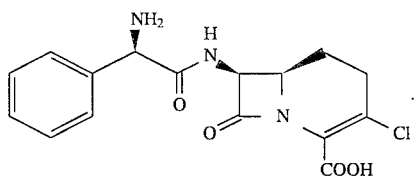
6. A compound of claim 5 which has the following x-ray diffraction pattern obtained with a nickel-filtered copper radiation of $\lambda=1.5406$ Å wherein d represents the innerplanar spacing and I/I$_1$ the relative intensity:
TABLE
| d | I/I$_1$ |
|---|---|
| 10.0767 | 100.00 |
| 9.7099 | 7.75 |
| 8.1380 | 3.96 |
| 7.5370 | 42.41 |
| 6.2587 | 5.54 |
| 5.8976 | 7.91 |
| 5.7412 | 17.72 |
| 5.6398 | 11.23 |
| 5.4127 | 3.80 |
| 5.2174 | 5.54 |
| 5.1075 | 45.41 |
| 4.9370 | 7.59 |
| 4.8905 | 9.49 |
| 4.5360 | 37.03 |
| 4.3921 | 12.34 |
| 4.2845 | 7.75 |
| 4.0913 | 11.55 |
| 3.7735 | 11.08 |
| 3.7132 | 16.46 |
| 3.6574 | 18.04 |
| 3.5853 | 21.36 |
| 3.5444 | 27.22 |
| 3.4696 | 7.59 |
| 3.3750 | 12.97 |
| 3.2862 | 14.72 |
| 3.2369 | 6.96 |
| 3.1533 | 10.76 |
| 3.0222 | 5.22 |
| 2.9859 | 6.01 |
| 2.9624 | 6.65 |
| 2.8638 | 6.49 |
| 2.8268 | 5.22 |
| 2.7363 | 6.96 |
| 2.6960 | 6.33 |
| 2.6186 | 6.01. |
* * * * *